(12) United States Patent
Ishihara

(10) Patent No.: US 8,743,190 B2
(45) Date of Patent: Jun. 3, 2014

(54) FLUOROSCOPY APPARATUS AND FLUOROSCOPY METHOD

(75) Inventor: Yasushige Ishihara, Tokyo (JP)

(73) Assignee: Olympus Corporation, Tokyo (JP)

( * ) Notice: Subject to any disclaimer, the term of this patent is extended or adjusted under 35 U.S.C. 154(b) by 484 days.

(21) Appl. No.: 12/725,900

(22) Filed: Mar. 17, 2010

(65) Prior Publication Data
US 2010/0245550 A1 Sep. 30, 2010

(30) Foreign Application Priority Data

Mar. 24, 2009 (JP) ................................. 2009-072846

(51) Int. Cl.
*A61B 1/06* (2006.01)

(52) U.S. Cl.
USPC .......................................................... 348/68

(58) Field of Classification Search
USPC .......................................................... 348/68
See application file for complete search history.

(56) References Cited

U.S. PATENT DOCUMENTS

| | | | |
|---|---|---|---|
| 5,879,284 A | 3/1999 | Tsujita | |
| 6,804,549 B2 * | 10/2004 | Hayashi | 600/431 |
| 2003/0001104 A1 * | 1/2003 | Sendai et al. | 250/458.1 |
| 2003/0013937 A1 * | 1/2003 | Tsujita et al. | 600/109 |
| 2005/0203423 A1 * | 9/2005 | Zeng et al. | 600/476 |
| 2008/0049215 A1 * | 2/2008 | Kawano et al. | 356/73 |

FOREIGN PATENT DOCUMENTS

| | | |
|---|---|---|
| JP | SHO 62-247232 | 10/1987 |
| JP | 10-165365 | 6/1998 |
| JP | 10-225426 A | 8/1998 |
| JP | 2006-266943 A | 10/2006 |
| JP | 2008-229026 A | 10/2008 |

* cited by examiner

*Primary Examiner* — Dave Czekaj
*Assistant Examiner* — Tracy Li
(74) *Attorney, Agent, or Firm* — Scully, Scott, Murphy & Presser, P.C.

(57) ABSTRACT

Unwanted information contained in a reference image is reduced, thus acquiring a fluorescence image having quantitative intensity information, regardless of the angle and distance of excitation light. The invention provides a fluoroscopy apparatus including an illumination portion that irradiates an observation target with illumination light containing excitation light; a first image-acquisition section that acquires a fluorescence image in a prescribed observation region of the observation target; a second image-acquisition section that acquires an out-of-focus reference image of the observation target in the observation region; and an image correction section that corrects the fluorescence image acquired by the first image-acquisition section using the reference image acquired by the second image-acquisition section.

18 Claims, 13 Drawing Sheets

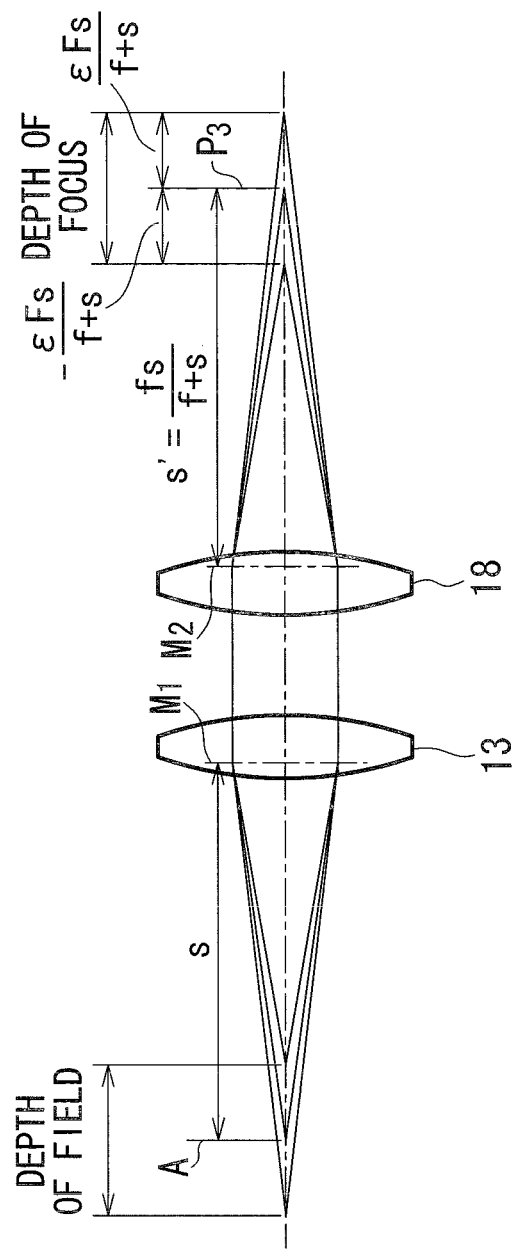

FLUOROSCOPY APPARATUS AND FLUOROSCOPY METHOD

BACKGROUND OF THE INVENTION

1. Field of the Invention

The present invention relates to a fluoroscopy apparatus and a fluoroscopy method.

This application is based on Japanese Patent Application No. 2009-072846, the content of which is incorporated herein by reference.

2. Description of Related Art

In fluoroscopy apparatuses, such as fluorescence endoscopes, in the related art, it is known that the intensity of generated fluorescence varies because the irradiation intensity of excitation light in an observation region varies depending on the angle and distance of the excitation light irradiating an observation target. To correct such variations in the fluorescence intensity, a known fluoroscopy apparatus corrects for the influence of distance and angle by dividing the acquired image by a reference image (for example, a reflected-light image etc.) acquired in the same observation region (for example, see Japanese Unexamined Patent Application, Publication No. SHO 62-247232).

However, because information other than distance and angle information, for example, image information of edges or blood vessel structures in the case where the observation target is biological tissue, is inevitably contained in the reference image, when correction is simply performed using this reference image, it is not possible to quantitatively perform correction over the entire image, and the image quality may deteriorate.

BRIEF SUMMARY OF THE INVENTION

An object of the present invention is to provide a fluoroscopy apparatus and a fluoroscopy method that can reduce unwanted information contained in a reference image to thus obtain a fluorescence image having quantitative intensity information, regardless of the angle and distance of the excitation light.

A first aspect of the present invention provides a fluoroscopy apparatus including an illumination portion configured to irradiate an observation target with illumination light containing excitation light; a first image-acquisition section configured to acquire a fluorescence image in a prescribed observation region on the observation target; a second image-acquisition section configured to acquire an out-of-focus reference image of the observation target in the observation region; and an image correction section configured to correct the fluorescence image acquired by the first image-acquisition section using the reference image acquired by the second image-acquisition section.

According to the aspect described above, when the observation target is irradiated with illumination light containing excitation light, emitted from the illumination portion, a fluorescent substance contained in the observation target is excited, generating fluorescence. The fluorescence generated in the prescribed observation region is acquired, in the form of a fluorescence image, by the first image-acquisition section. The returning light from the same observation region is acquired, in the form of a reference image, by the second image-acquisition section. The fluorescence image is corrected by the image correction section using the reference image obtained by capturing the same observation target, thereby making it possible to obtain a quantitative fluorescence image in which fluorescence intensity variations that depend on the distance and angle of the illumination light are corrected.

In this case, because the reference image acquired by the second image-acquisition section is an out-of-focus image of the observation target, the optical resolution is degraded, information about the surface condition etc. of the observation target is lost, and information about intensity variations based on the angle and distance of the illumination light is contained. Therefore, even if correction is performed using this reference image, it is possible to reduce the amount of information about the surface condition etc. of the observation target contained in the corrected fluorescence image, and it is thus possible to acquire a high-precision fluorescence image having quantitative intensity information.

In the aspect described above, the image correction section preferably divides the fluorescence image by the reference image.

By doing so, it is possible to obtain a fluorescence image having high quantitativeness with a simple calculation.

In the aspect described above, the second image-acquisition section may include an image-acquisition device configured to acquire the reference image, and an image-acquisition optical system configured to focus light returning from the observation target; and an image-acquisition surface of the image-acquisition device may be disposed at a position shifted in an optical axis direction relative to a focal position of the image-acquisition optical system.

With this configuration, it is possible to acquire an out-of-focus reference image merely by shifting the focal position; therefore, it is not necessary to perform complex image processing, and thus the amount of processing and time required for the calculation can be reduced. Moreover, there is no need to employ a special optical system, and it is thus possible to acquire a high-precision fluorescence image with a simple configuration.

The aspect described above may further include a moving mechanism configured to move the image-acquisition optical system or the image-acquisition device in the optical axis direction.

By doing so, it is possible to vary the degree to which the resolution of the reference image is reduced, and a suitable reference image can be selected.

In the aspect described above, the illumination portion may irradiate the observation target simultaneously with white light and excitation light, serving as the illumination light; the fluoroscopy apparatus may further include a light-collecting lens configured to collect the return light returning from the observation target; a first splitting portion configured to split fluorescence and white light from the returning light collected by the light-collecting lens; a second splitting portion configured to further split the white light split by the first splitting portion; a white-light image-acquisition optical-system configured to focus one of the white light beams split by the second splitting portion; and a white-light image-acquisition device whose image-acquisition surface is disposed at a focal position of the white-light image-acquisition optical system; wherein the fluorescence split by the first splitting portion may be guided to the first image-acquisition section, and wherein the other white light beam split by the second splitting portion or light in part of a wavelength band of the other white light beam may be guided to the second image-acquisition section.

With this configuration, when the observation target is simultaneously irradiated with white light and excitation light, a fluorescent substance contained inside the observation target is excited, generating fluorescence, and the white light is reflected at the surface of the observation target. Regarding the fluorescence and the white light returning from the observation target, the fluorescence split by the first splitting portion after being collected by the light-collecting lens is acquired in the form of a fluorescence image by the first image-acquisition section.

On the other hand, the white light split by the first splitting portion is further split into two beams by the second splitting portion, and one of the beams is acquired in the form of a white-light image by the white-light image acquisition device via the white-light image acquisition optical system. The other white-light beam is guided to the second image-acquisition section and is acquired in the form of an out-of-focus reference image. Accordingly, it is possible to simultaneously acquire a white-light image that shows the surface condition of the observation target and a high-precision corrected fluorescence image.

In the aspect described above, the second image-acquisition section may include a reference-light image-acquisition optical system whose focal position is shifted in the optical axis direction relative to the image-acquisition surface of the white-light image-acquisition device.

By doing so, it is possible to acquire a white-light image and a reference image in different regions of the same white-light image-acquisition device. Therefore, a separate image-acquisition device need not be provided for the reference image, thus simplifying the configuration.

In the aspect described above, the illumination portion may irradiate the observation target with white light and excitation light, serving as the illumination light, in a time-division manner; the fluoroscopy apparatus may further in lode a light-collecting lens configured to collect the return light returning from the observation target; and a splitting portion configured to split the return light collected by the light-collecting lens into two; wherein one of the returning light beams split by the splitting portion may be guided to the first image-acquisition section; wherein the other returning light beam split by the splitting portion may be guided to the second image-acquisition section; and wherein the first image-acquisition section may acquire a white-light image when the white light is radiated from the illumination portion and may acquire a fluorescence image when the excitation light is radiated from the illumination portion.

With this configuration, it is possible to acquire a white-light image and a fluorescence image in a time-division manner with the same image-acquisition device in the first image-acquisition section, and it is possible to acquire a reference image with the separate image-acquisition device in the second image-acquisition section. Therefore, two image-acquisition devices for acquiring the white-light image and the corrected fluorescence image are used, thus simplifying the configuration.

In the aspect described above, the illumination portion may irradiate the observation target with white light and excitation light, serving as the illumination light, in a time-division manner; the fluoroscopy apparatus may further include: a light-collecting lens configured to collect the returning light returning from the observation target; and a splitting portion configured to split the returning light collected by the light-collecting lens into white light and fluorescence; wherein the fluorescence split by the splitting portion may be guided to the first image-acquisition section; wherein the white light split by the splitting portion may be guided to the second image-acquisition section; and wherein the second image-acquisition section may include an image-acquisition device configured to acquire the reference image and a white-light image, an image-acquisition optical system configured to focus the white light returning from the observation target, and a switching mechanism configured to selectively switch the focal position of the image-acquisition optical system between a position in alignment with and a position shifted relative to an image-acquisition surface of the image-acquisition device when the white light is radiated by the illumination portion.

With this arrangement, an in-focus white-light image and an out-of-focus reference image can be acquired in a time-division manner in the second image-acquisition section by operating the switching mechanism at the timing at which white light is radiated from the illumination portion to serve as illumination light. Then, a fluorescence image can be acquired in the first image-acquisition section at the timing at which excitation light is radiated from the illumination portion to serve as the illumination light. Accordingly, two image-acquisition devices for acquiring the white-light image and the corrected fluorescence image are used, thus simplifying the configuration.

In the aspect described above, the switching mechanism may be a moving mechanism configured to move the image-acquisition optical system or the image-acquisition device in the optical axis direction.

By doing so, the image-acquisition optical system or the image-acquisition device is moved in the optical axis direction by the moving mechanism, making it possible to easily and selectively switch between states where the focal position of the image-acquisition optical system is aligned with and shifted relative to the image-acquisition surface of the image-acquisition device.

In the aspect described above, the image-acquisition optical system may be a liquid-crystal lens.

With this configuration, merely by changing the voltage applied to the liquid crystal lens, it is possible to easily and selectively switch between states where the focal position of the image-acquisition optical system is aligned with and shifted relative to the image-acquisition surface of the image-acquisition device.

In the aspect described above, the illumination portion may irradiate the observation target with white light and excitation light simultaneously; the fluoroscopy apparatus may further include: an image-acquisition optical system configured to focus returning light returning from the observation target; a filter portion that selectively transmits the reference light, the white light or fluorescence in the returning light; an image-acquisition device configured to acquire the white light or the fluorescence transmitted through the filter portion; a switching mechanism configured to switch between a position where the focal position of the image-acquisition optical system is aligned with an image-acquisition surface of the image-acquisition device when the white light is transmitted by the filter portion, and a position where the focal position of the image-acquisition optical system is shifted relative to the image-acquisition surface of the image-acquisition device when the reference light is transmitted; and an image correction section configured to correct the fluorescence image acquired by the image-acquisition device using the reference image acquired with the reference light is transmitted by the switching mechanism.

According to the above-described aspect, it is possible to acquire an in-focus white-light image and an out-of-focus reference image in a time-division manner by operating the switching mechanism at the timing at which the filter portion transmits the white light. Then, it is possible to acquire a fluorescence image in the first image-acquisition section at the timing at which the filter portion transmits the fluorescence. Accordingly, just one image-acquisition device for acquiring the white-light image and the corrected fluorescence image is used, thus further simplifying the configuration.

Another aspect of the present invention provides a fluoroscopy method including an illumination step of irradiating an observation target with illumination light containing excitation light; a fluorescence-image acquisition step of acquiring a fluorescence image in a prescribed observation region of the observation target; a reference-image acquisition step of acquiring an out-of-focus reference image of the observation target in the observation region; and an image correcting step of correcting the fluorescence image acquired in the fluorescence-image acquisition step using the reference image acquired in the reference-image acquisition step.

According to the above-described aspect, the illumination light is radiated in the illumination step, fluorescence in the returning light returning from the observation target is acquired in the form of a fluorescence image in the fluorescence-image acquiring step, and the reflected light etc. in the returning light is acquired in the form of a reference image in the reference-image acquiring step. Then, in the image correcting step, the fluorescence image is corrected by using the reference image. Because the reference image is an out-of-focus image of the observation target, the optical resolution is degraded, information about the surface condition etc. of the observation target is lost, and information about the intensity variation based on the angle and distance of the illumination light is contained. Therefore, even if correction is performed using this reference image, it is possible to reduce the amount of information about the surface condition of the observation target contained in the corrected fluorescence image, and it is thus possible to acquire a high-precision fluorescence image having quantitative intensity information.

The present invention affords an advantage in that unwanted information contained in the reference image can be reduced, which makes it possible to acquire a fluorescence image having quantitative intensity information regardless of the angle and distance of the excitation light.

BRIEF DESCRIPTION OF THE SEVERAL VIEWS OF THE DRAWINGS

FIG. 3 is a diagram for explaining a shift in focal position in an image-acquisition device for acquiring a reference image, in the fluoroscopy apparatus in FIG. 1, in a case where an objective lens having a finite depth of field is used.

DETAILED DESCRIPTION OF THE INVENTION

A fluoroscopy apparatus according to a first embodiment of the present invention will be described below with reference to the drawings.

Figure 1:
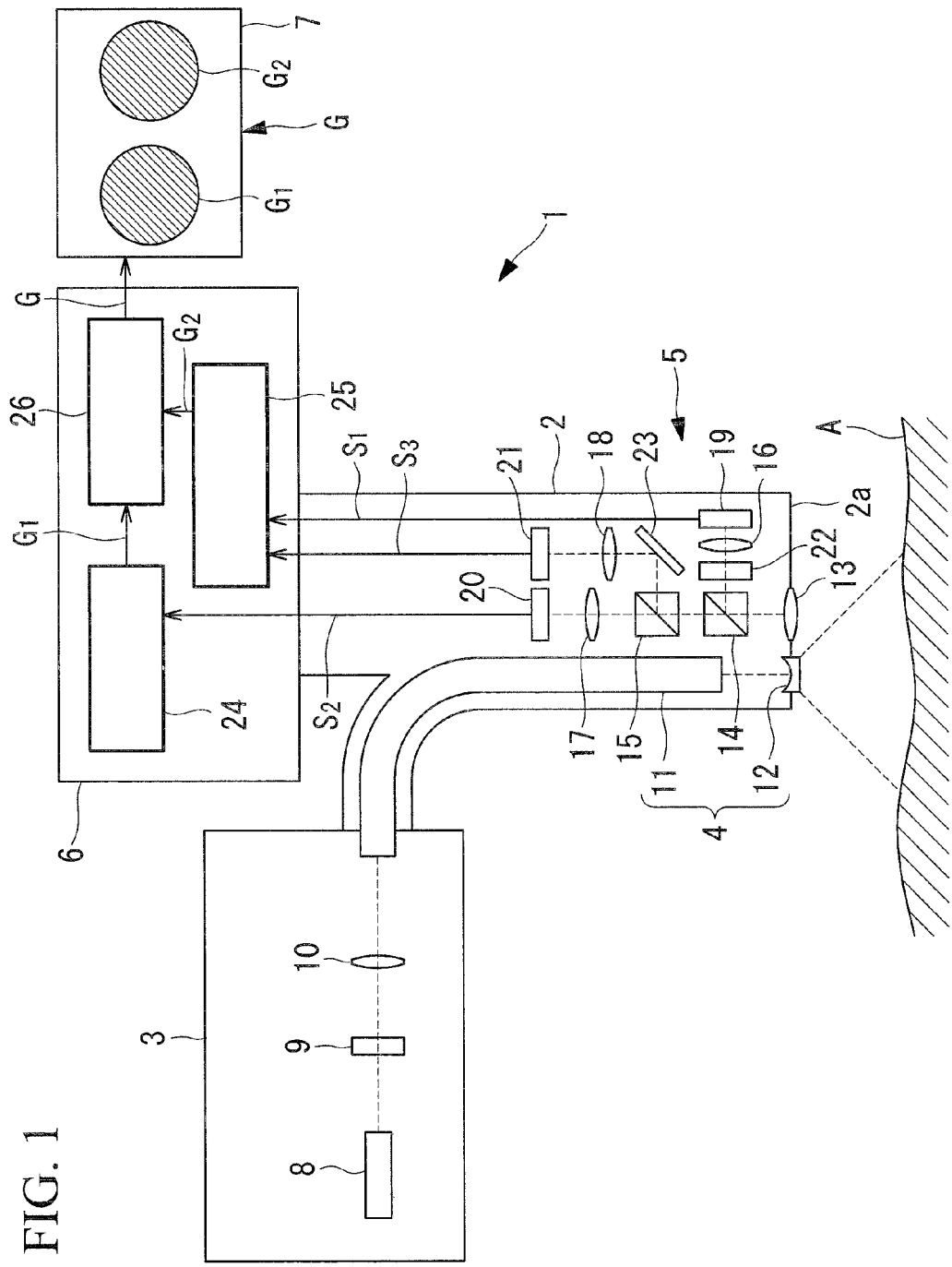
FIG. 1 is a diagram showing the overall configuration of a fluoroscopy apparatus according to a first embodiment of the present invention.

As shown in FIG. 1, a fluoroscopy apparatus 1 according to this embodiment, which is an endoscope apparatus, includes a long, thin inserted portion 2 that is inserted inside a body; a light source (illumination portion) 3; an illumination unit (illumination portion) 4 that radiates illumination light coming from the light source 3 onto an observation target A from the end of the inserted portion 2; an image-acquisition unit 5 that is provided at the end of the inserted portion 2 and that acquires image information of biological tissue, i.e. the observation target A; an image processing unit 6 that is disposed at the base end of the inserted portion 2 and that processes the image information acquired by the image-acquisition unit 5; and a monitor 7 that displays an image G processed by the image processing unit 6.

The light source 3 includes a xenon lamp 8; a filter 9 that extracts white light containing excitation light (a wavelength band of 400 to 740 nm) from the illumination light emitted from the xenon lamp 8; and a coupling lens 10 that focuses the white light containing excitation light, extracted by the filter 9.

The illumination unit 4 includes a light guide fiber 11 that is disposed along substantially the entire lengthwise direction of the inserted portion 2 and that guides the white light containing excitation light, focused by the coupling lens 10; and an illumination optical system 12 that is disposed at the end of the inserted portion 2 and that expands the white light containing excitation light guided by the light guide fiber 11 to irradiate the observation target A, which is opposite an end face 2a of the inserted portion 2.

The image-acquisition unit 5 includes an objective lens 13 that collects light returning from a prescribed observation region on the observation target A; a dichroic mirror (splitting portion) 14 that reflects light at or above the excitation wavelength (excitation light and fluorescence) and transmits white light with a wavelength shorter than the excitation wavelength, contained in the returning light collected by the objective lens 13; a half mirror 15 that further splits the white light transmitted through the dichroic mirror 14 into two; three focusing lenses (image-acquisition optical system) 16 to 18 that respectively focus the fluorescence reflected by the dichroic mirror 14 and the two white light beams split by the half mirror 15; and three image-acquisition devices 19 to 21, such as CCDs, that acquire the fluorescence and the two white light beams focused by the focusing lenses 16 to 18. Reference numeral 22 in the figure is an excitation-light cutting filter that blocks excitation light from the light reflected by the dichroic mirror 14 (for example, it transmits only light in the wavelength band 760 to 850 nm), and reference numeral 23 is a mirror.

Figure 2:
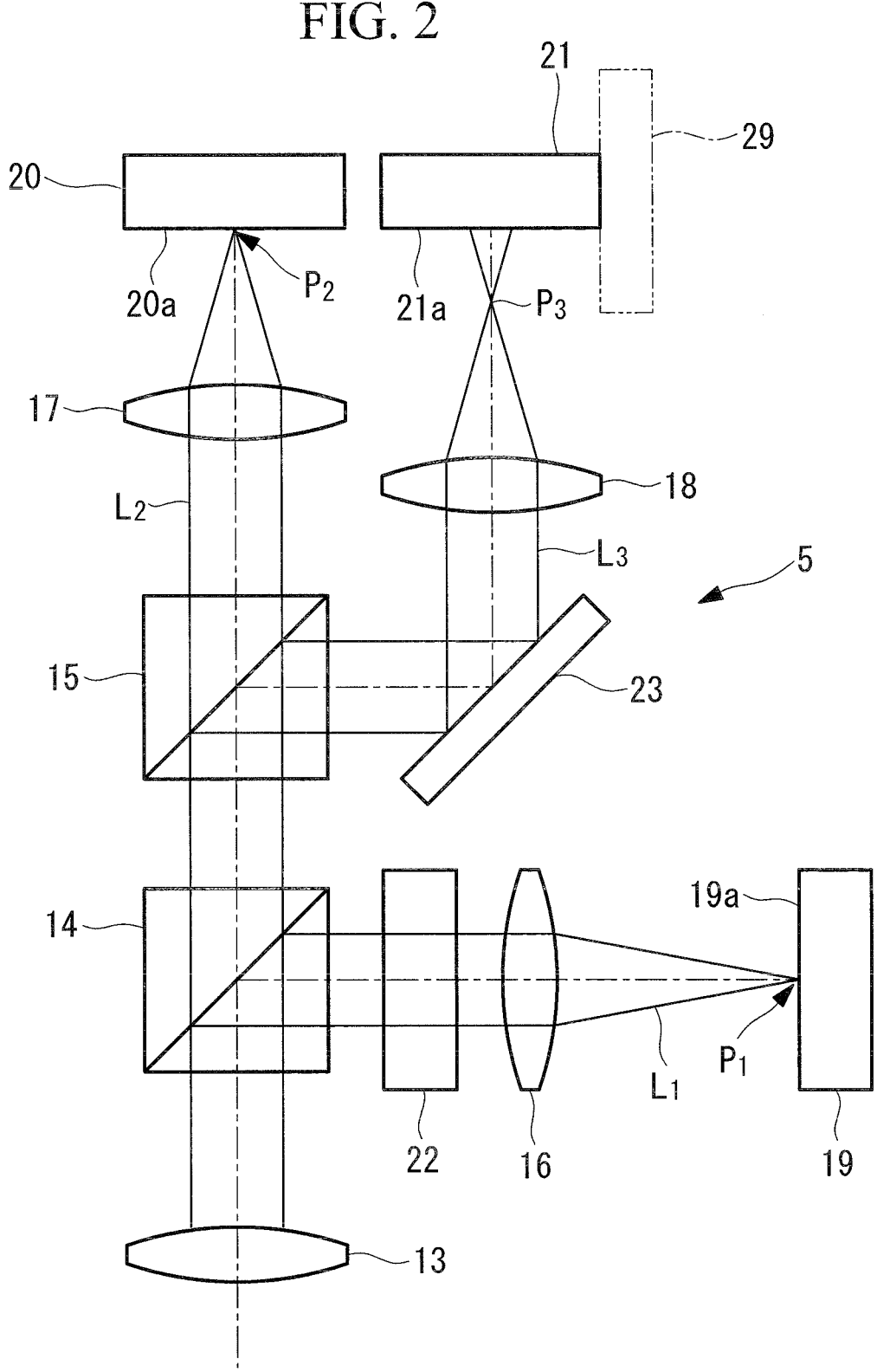
FIG. 2 is a schematic diagram showing an image-acquisition unit in the fluoroscopy apparatus in FIG. 1.

As shown in FIG. 2, focal positions $P_1$ and $P_2$ of the focusing lens 16 that focuses fluorescence $L_1$ and the focusing lens 17 that focuses one of the white light beams $L_2$ are aligned with image-acquisition surfaces 19a and 20a of the corresponding image-acquisition devices 19 and 20. As for the focusing lens 18 that focuses the other white light beam $L_3$, the focal position $P_3$ thereof is located at a position shifted in the optical axis direction relative to an image-acquisition surface 21a of the corresponding image-acquisition device 21. Accordingly, fluorescence image information $S_1$ and white-light image information $S_2$ that are in-focus on the observation target A are acquired by the image-acquisition devices 19 and 20, and reference image information $S_3$ that is out-of-focus on the observation target A is acquired by the image-acquisition device 21.

As shown by the broken lines in FIG. 2, a moving mechanism for moving the image-acquisition device 21 or the focusing lens 18 in the optical axis direction may be provided. Doing so allows the amount of shift of the focal position $P_3$ to be adjusted to an appropriate value.

The image-processing unit 6 includes a reflected-light image generating unit 24 that generates a reflected-light image $G_1$ from the in-focus white-light image information $S_2$ acquired by the image-acquisition device 20, a corrected fluorescence-image generating unit 25 that generates a fluorescence image $G_2$ that is corrected on the basis of the fluorescence image information $S_1$ acquired by the image-acquisition device 19 and the reference image information $S_3$ acquired by the image-acquisition device 21, and an image-combining unit 26 that generates an image G formed by combining these images.

The corrected fluorescence-image generating unit 25 generates the corrected fluorescence image by dividing the fluorescence image information $S_1$ by the out-of-focus white-light image information $S_3$ at each pixel.

The image-combining unit 26 combines the images so that, for example, the reflected-light image and the corrected fluorescence image are simultaneously displayed side-by-side on the monitor 7, and the combined image is output to the monitor 7.

For example, a fluorescence image obtained with Cy7 fluorescent dye may be used as the fluorescence image $G_2$. In particular, if a fluorescent agent formed by binding, for example, Cy7 and an antibody to the cancer-specific molecule CEA (Anti-CEA antibody) is administered in advance to the observation target A, it is possible to acquire a tumor-specific fluorescence image $G_2$.

The operation of the thus-configured fluoroscopy apparatus 1 according to this embodiment will be described below.

To observe biological tissue inside a body, that is, the observation target A, using the fluoroscopy apparatus 1 according to this embodiment, the inserted portion 2 is inserted inside the body, and the end face 2a of the inserted portion 2 is made to face the observation target A. Then, the light source 3 is operated to emit white light containing excitation light, which is introduced into the light guide fiber 11 by the coupling lens 10. The white light containing excitation light that is guided inside the light guide fiber 11 to reach the end of the inserted portion 2 is expanded by the illumination optical system 12 at the tip of the inserted portion 2 and is radiated onto the observation target A (illumination step).

A fluorescent substance contained in the observation target A is excited by the excitation light, generating fluorescence, and white light is reflected at the surface of the observation target A. The fluorescence and reflected white light (returning light) return to the end face 2a of the inserted portion 2 from the observation target A, and part of the returning light emitted from inside the observation region is collected by the objective lens 13.

The returning light collected by the objective lens 13 is split into each wavelength by the dichroic mirror 14, and returning light containing the excitation wavelength and the fluorescence $L_1$, for example, light in the wavelength band 700 nm to 850 nm, is reflected by the dichroic mirror 14. Then, after the excitation light (for example, light at 740 nm or less) is removed by the excitation light cutting filter 22, only the fluorescence $L_1$ is focused by the focusing lens 16 and is acquired by the image-acquisition device 19 as the fluorescence image information $S_1$ (fluorescence-image acquisition step).

In addition, of the returning light collected by the objective lens 13, the light transmitted through the dichroic mirror 14, for example, white light in the wavelength band 400 nm to 700 nm, is split into two by the half mirror 15. One white light beam $L_2$ is acquired as the white-light image information $S_2$ by the image-acquisition device 20 while focused by the focusing lens 17, and the other white light beam $L_3$ is converged to an out-of-focus state by the focusing lens 18 and is acquired as the reference image information $S_3$ by the image-acquisition device 21 (reference-image acquisition step).

The image information $S_1$ to $S_3$ acquired by the respective image-acquisition devices 19 to 21 are sent to the image-processing unit 6, where the white-light image information $S_2$ is input to the reflected-light image generating unit 24 to generate the reflected-light image $G_1$. On the other hand, the fluorescence image information $S_1$ and the reference image information $S_3$ are input to the corrected fluorescence-image generating unit 25, where the corrected fluorescence image $G_2$ is generated by dividing the fluorescence image information $S_1$ by the reference image information $S_3$ at each pixel (image correcting step).

In this case, because the illumination light is expanded by the illumination optical system 12 and is radiated to each position on the observation target under different angle and distance conditions, the intensity of the excitation light radiating each position differs; therefore, the fluorescence image information $S_1$ contains intensity variations that depend on the distance and angle of the illumination light. In other words, even though it is assumed that the same fluorescent substance is uniformly contained at all positions, actually, the intensity of the fluorescence $L_1$ produced differs depending on the angle and the distance of the illumination light.

On the other hand, because the reference image information $S_3$ is acquired for the same observation region under the same illumination-light radiation conditions as the fluorescence image information $S_1$, information about the variations in intensity due to the distance and angle of the illumination light contains the same information as the fluorescence image information $S_1$. Furthermore, in this embodiment, because the reference image information $S_3$ is acquired by shifting the focal position $S_3$ of the focusing lens 18 in the optical axis direction relative to the image-acquisition surface 21a of the image-acquisition device 21, the resolution thereof is reduced, and the amount of information about the surface condition of the observation target A is decreased.

The amount of shift of the focal position $P_3$ of the focusing lens 18 will now be described. In this embodiment, for any assumed observation distance, it is necessary to shift the focusing lens 18 or the image-acquisition device 21 to a position where the image-acquisition surface 21a of the image-acquisition device 11 is not inside the depth of focus of the focusing lens 18.

More specifically, when the objective lens 13 has a finite depth of field, as shown in FIG. 3, where s is the distance from the principal plane $M_1$ of the objective lens 13 to the observation target A, s' is the distance from the principal plane $M_2$ of the focusing lens 18 to the focal position $P_3$, $\epsilon$ is the diameter of a permissible circle of confusion, f is the focal length, and F is the F-number, the distance s' is given by s'=fs/(f+s), and the depth of focus of the focusing lens 18 is $+\epsilon Fs/(f+s)$. Therefore, by disposing the image-acquisition surface 21a at a position s'$-\epsilon$Fs/(f+s) closer to the focusing lens 18 or at a position s'$+\epsilon$Fs/(f+s) farther away from the focusing lens 18, it is possible to dispose the image-acquisition device 21 at a position where the image-acquisition surface 21a is not in the depth of focus of the focusing lens 18.

Figure 4A:
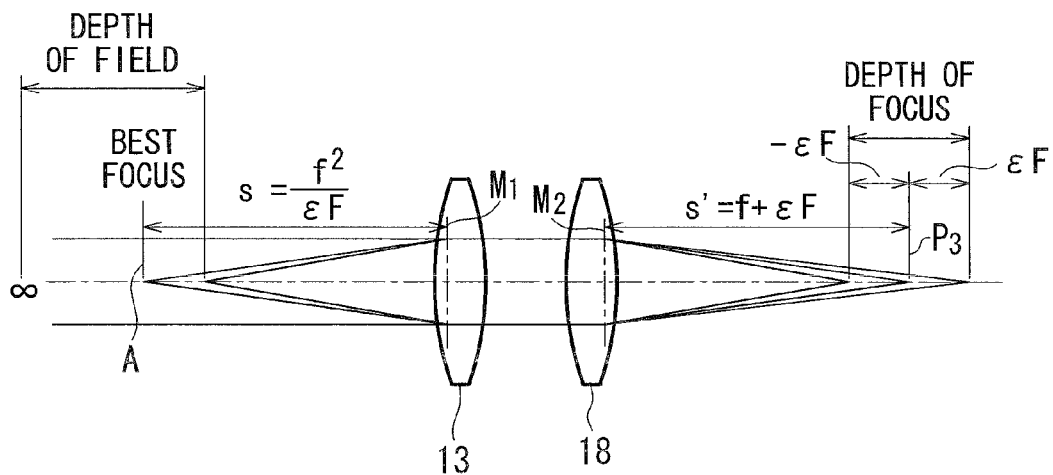
FIG. 4A is a diagram, similar to FIG. 3, for explaining the depth of focus of a focusing lens at a best-focus position in a case where an objective lens having an infinite depth of field is used.

If the objective lens 13 has a depth of field that extends to infinity, as shown in FIG. 4A, at the best-focus position, $s=f^2/\epsilon F$ and s'=f+$\epsilon$F, and the depth of focus of the focusing lens 18 is $\pm \epsilon$F relative to the position s'.

Figure 4B:
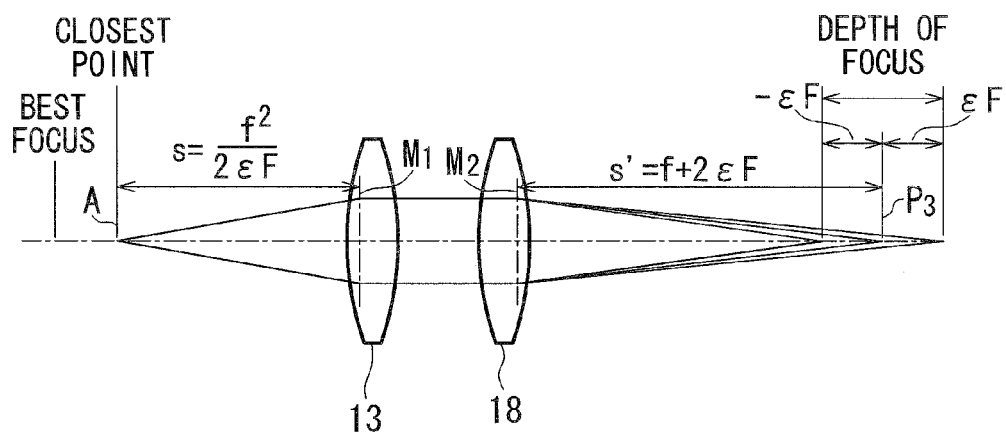
FIG. 4B is a diagram, similar to FIG. 3, for explaining the depth of focus of a focusing lens at a closest point in a case where an objective lens having an infinite depth of field is used.

At the closest point, on the other hand, as shown in FIG. 4B, the depth of focus of the focusing lens 18 is $\pm \epsilon$F relative to the position s'=f+2$\epsilon$F; therefore, it is necessary to dispose the image-acquisition surface 21a at a position f+3$\epsilon$F away from the principal plane of the focusing lens 18.

Figure 4C:
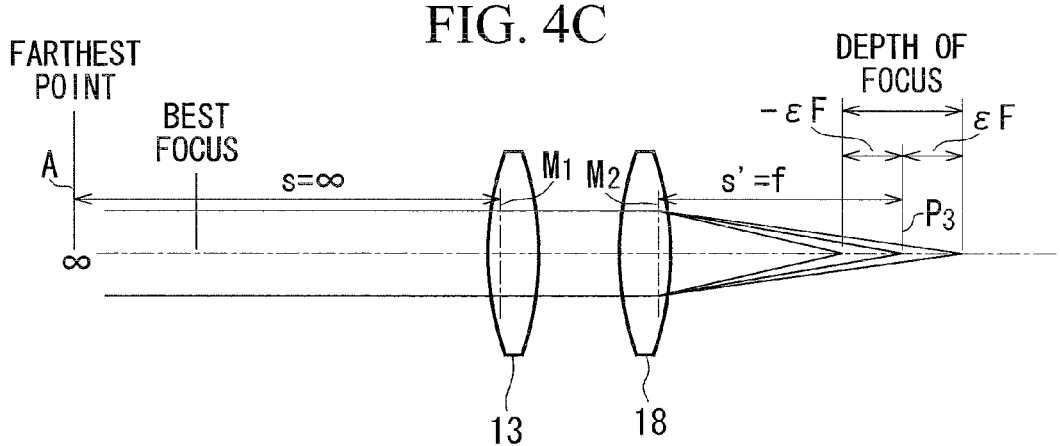
FIG. 4C is a diagram, similar to FIG. 3, for explaining the depth of focus of a focusing lens at a farthest point in a case where an objective lens having an infinite depth of field is used.

At infinity, i.e. the farthest point, as shown in FIG. 4C, the depth of focus of the focusing lens is $\pm$Fs relative to the position s'=f; therefore, it is necessary to dispose the image-acquisition surface 21a at a position a distance f$-\epsilon$F closer to the focusing lens 18 from the principal plane $M_2$ of the focusing lens 18.

Therefore, when the objective lens 13 has a depth of field that extends to infinity, by placing the image-acquisition surface 21a of the image-acquisition device 21 either a distance f$-\epsilon$F closer to the principal plane $M_2$ of the focusing lens 18 or a distance f+3$\epsilon$F farther away from the principal plane $M_2$ of the focusing lens 18, it is possible to acquire the out-of-focus reference image information $S_3$ for any assumed observation conditions.

Thus, with the fluoroscopy apparatus 1 according to this embodiment, even assuming that there are blood vessel structures and various characteristically shaped portions on the surface of the observation target A, information about such characteristically shaped portions is removed from the acquired reference image information $S_3$, leaving information about intensity changes based on the angle and distance of the illumination light. As a result, by correcting the fluorescence image information $S_1$ using the reference image information $S_3$ obtained in this way, it is possible to obtain the fluorescence image $G_2$ with high quantitativeness, corrected to the same state as when excitation light is radiated under uniform conditions, regardless of the angle and distance of the excitation light.

In addition, with the fluoroscopy apparatus 1 according to this embodiment, it is possible to obtain the low-resolution reference image information $S_3$ containing information about the intensity variations based on the angle and distance of the illumination light, merely by shifting the focal position $P_3$ of the focusing lens 18. Therefore, because special optical elements or computational processing is not required, an advantage is afforded in that it is possible to obtain the fluorescence image $G_2$ having high quantitativeness rapidly and with a simple configuration.

Note that, in this embodiment, a description has been given of a case where the image-acquisition device 20 for acquiring the white-light image information $S_2$ and the image-acquisition device 21 for acquiring the reference image information $S_3$ are separately provided. Instead of this, however, as shown in FIG. 5, the white-light image information $S_2$ and the reference image information $S_3$ may both be acquired using different regions of the same image-acquisition device 20'.

Figure 5:
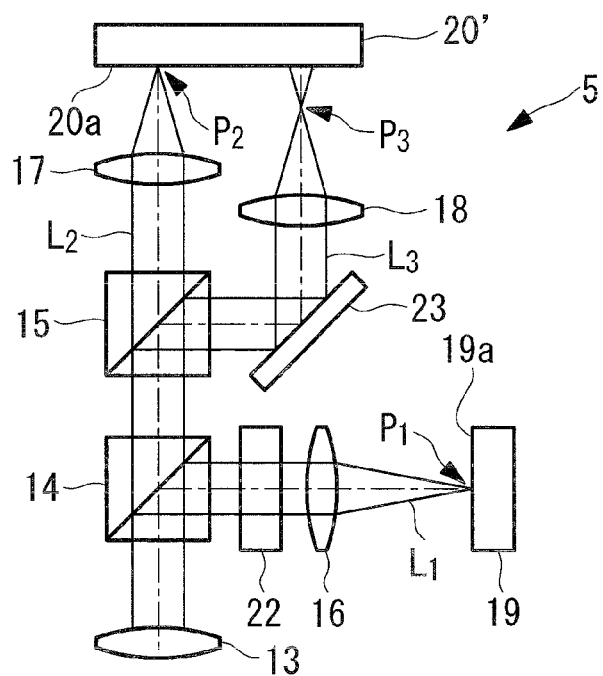
FIG. 5 is a schematic diagram showing a first modification of the image-acquisition unit in the fluoroscopy apparatus in FIG. 1.
Figure 6:
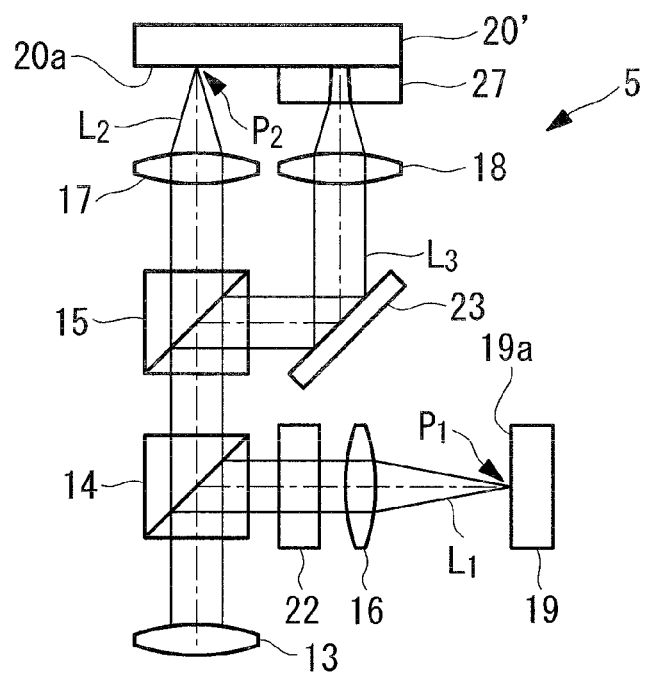
FIG. 6 is a schematic diagram showing a second modification of the image-acquisition unit in the fluoroscopy apparatus in FIG. 1.

In this case, as shown in FIG. 5, one of the focusing lenses, namely, the focusing lens 18, may be disposed at a different position in the optical axis direction from the other focusing lens 17. Alternatively, as shown in FIG. 6, the positions of the focusing lenses 17 and 18 relative to the image-acquisition device 20' may be the same, and an optical element such as a parallel flat glass plate 27 may be disposed only in the space between the image-acquisition device 20' and one of the focusing lenses, i.e., the focusing lens 18. Also, a focusing lens having a different focal length from the focusing lens 17 may be used as the focusing lens 18.

Figure 7:
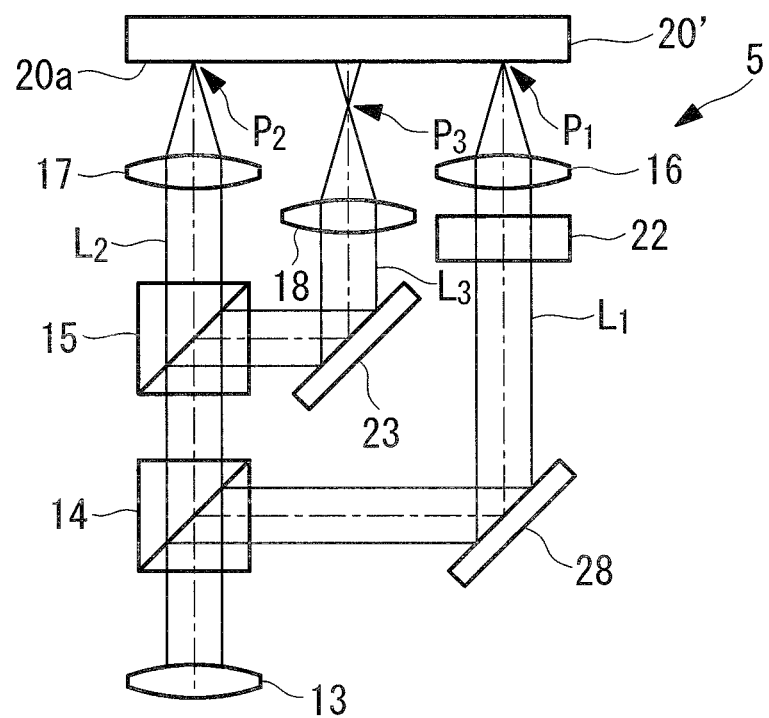
FIG. 7 is a schematic diagram showing a third modification of the image-acquisition unit in the fluoroscopy apparatus in FIG. 1.

As shown in FIG. 7, the fluorescence $L_1$ reflected by the dichroic mirror 14 may be focused on another region of the same image-acquisition device 20', thus allowing the fluorescence image information $S_1$, the white-light image information $S_2$, and the reference image information $S_3$ to all be acquired with the single image-acquisition device 20'. Reference numeral 28 in the figure is a mirror.

It has been assumed that the returning light is collected by a single objective lens 13; instead of this, however, two separate objective lenses 13 may be provided for collecting white light and fluorescence.

The reference image information $S_3$ may be based on light other than white light. For example, in FIG. 2, an optical filter (not shown) that transmits only specific wavelengths may be provided between the focusing lens 18 and the mirror 23. By doing so, it is possible to freely set the band of light that serves as the basis of the reference image information $S_3$ For example, the transmission band of the optical filter can also be restricted to red light (for example, 600 nm to 700 nm). Thus, by selecting a band in which absorption by blood is small, it is possible to reduce the inclusion of information about blood vessel structures in the reference image.

Next, a fluoroscopy apparatus 30 according to a second embodiment of the present invention will be described below with reference to the drawings.

In the description of this embodiment, parts having the same configuration as those in the fluoroscopy apparatus 1 according to the first embodiment described above will be assigned the same reference numerals, and a description thereof will be omitted.

Figure 8:
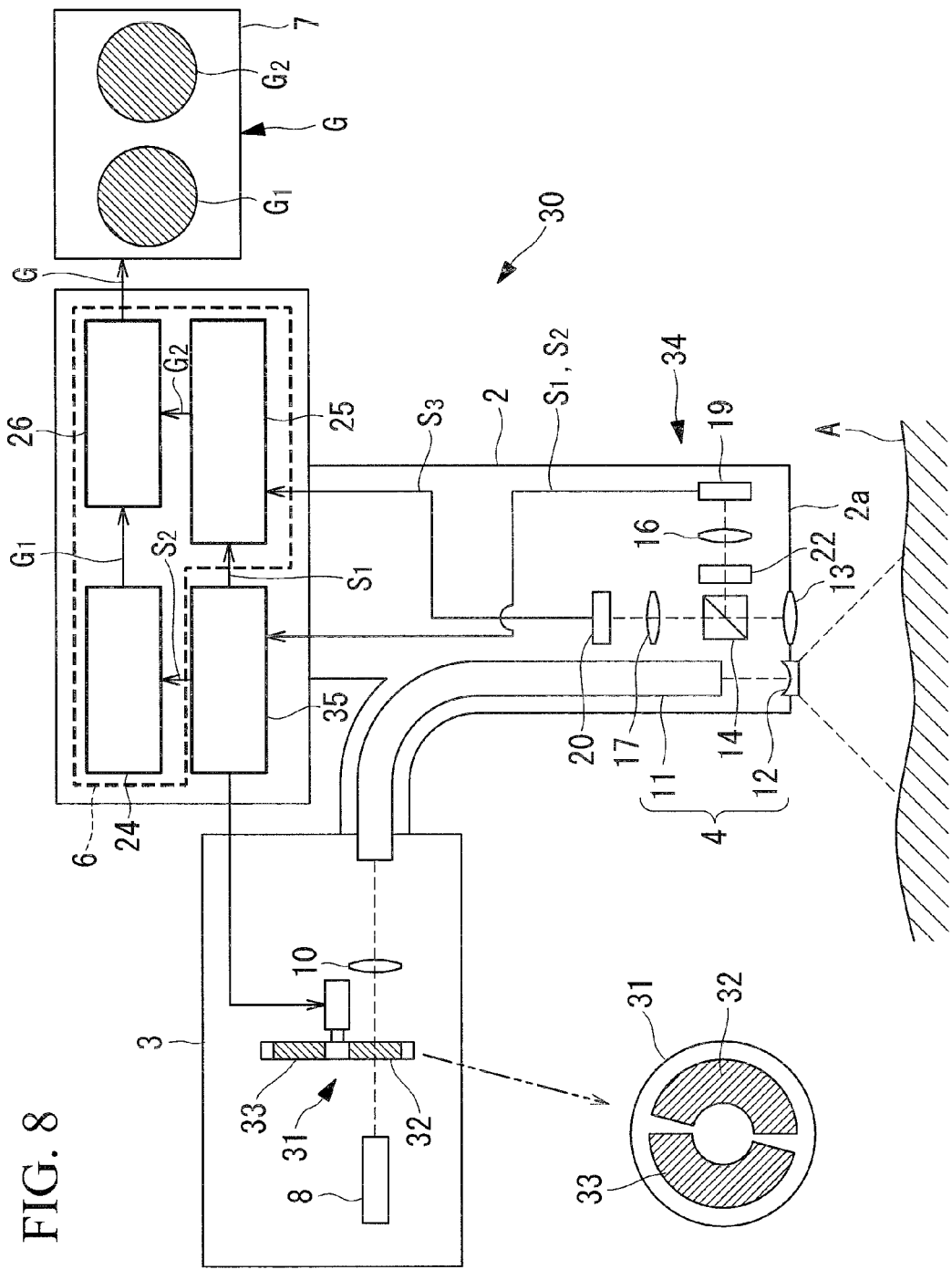
FIG. 8 is a diagram showing the overall configuration of a fluoroscopy apparatus according to a second embodiment of the present invention.

As shown in FIG. 8, the fluoroscopy apparatus 30 according to this embodiment is provided with a filter turret 31 in the light source 3. The filter turret 31 is formed in a circular plate shape and includes a plurality of filters 32 and 33 with different wavelength characteristics, disposed in the circumferential direction, and is rotated about the rotational axis thereof by a motor 10. The filter 32 transmits white light (for example, light in the wavelength band 400 nm to 700 nm), and the filter 33 transmits excitation light (for example, light in the wavelength band 650 nm to 740 nm). Accordingly, the different filters 32 and 33 are alternately disposed on the optical axis of the illumination light from the xenon lamp 8, and therefore, it is possible to introduce the excitation light and the white light into the light guide fiber in a time-division manner.

Another difference between the fluoroscopy apparatus 30 according to this embodiment and the fluoroscopy apparatus 1 according to the first embodiment is an image-acquisition unit 34. In the image-acquisition unit 34, an element having, for example, a transmittance of approximately 50% (a reflectance of approximately 50%) for white light (wavelengths of substantially 400 nm to 700 nm) and a transmittance of approximately 0% (a reflectance of approximately 100%) for fluorescence (the wavelength band 760 nm to 850 nm) is used as the dichroic mirror 14. After the dichroic mirror 14, the half mirror 15 that splits the white light is not provided, and only the single focusing lens 17 and the single image-acquisition 20 are provided. In this embodiment, the image-acquisition device 20 that captures white light is disposed at a position where the focal position of the focusing lens 17 is shifted in the optical axis direction relative to the image-acquisition surface 20a. The reference image information $S_3$, which is the output from this image-acquisition device 20, is to the corrected fluorescence-image generating unit 25 in the image processing unit 6.

The excitation light cutting filter 22 blocks the excitation light (for example, light in the wavelength band 650 nm to 740 nm) and transmits substantially 100% of the fluorescence (for example, light in the wavelength band 760 nm to 850 nm), and transmits a small amount (for example, approximately 5%) of white light excluding the excitation light band (for example, light from 400 nm to 650 nm). The fluoroscopy apparatus 30 according to this embodiment is provided with a switching controller 35 that allocates the fluorescence image information $S_1$ and the white-light image information $S_2$ output from the image-acquisition device 19 to the reflected-light image generating unit 24 and the corrected fluorescence-image generating unit 25 in synchronization with the rotation of the filter turret 31. In other words, in the filter turret 31, when the filter 33 that transmits excitation light is disposed on the optical axis from the xenon lamp 8, the switching controller 35 outputs the fluorescence image information $S_1$, which is output from the image-acquisition device 19, to the corrected fluorescence-image generating unit 25.

On the other hand, in the filter turret 31, when the filter 32 that transmits white light is disposed on the optical axis, the switching controller 35 outputs the white-light image information $S_2$, which is output from the image-acquisition device 19, to the reflected-light image generating unit 24. At this time, only about 2.5% of the white light (light in the wavelength band 400 nm to 650 nm) serving as the basis of the white-light image information $S_2$ reaches the image-acquisition device 19 because of the 50% reflectance of the dichroic mirror 14 and the 5% transmittance of the excitation light cutting filter 22; however, because a high-sensitivity device is used for the image-acquisition device 19, which is for observing fluorescence, it is possible to adequately observe even white light that is transmitted at approximately just 2.5%.

A reflected-light image $G_1$ is generated in the reflected-light image generating unit 24 on the basis of the white-light image information $S_2$ sent thereto. The corrected fluorescence-image generating unit 25, upon receiving the fluorescence image information $S_1$, temporarily stores it, and once the reference image information $S_3$ is received when the filter 32 is on the optical axis, the stored fluorescence image information $S_1$ is divided by the received reference image information $S_3$ at each pixel so as to generate the corrected fluorescence image $G_2$.

Thus, with the fluoroscopy apparatus 30 according to this embodiment, because the fluorescence image information $S_1$ and the white-light image information $S_2$ are acquired in a time-division manner, the number of image-acquisition devices 19 and 20 can be reduced, thus simplifying the construction.

Note that in this embodiment, the filter turret 31 includes two filters, namely, the filter 32 that transmits white light and the filter 33 that transmits excitation light. In addition to these, however, the filter turret 31 may include a reference filter (not shown) that transmits reference illumination light (for example, 600 nm to 700 nm). In other words, when the filter 33 is on the optical axis, the switching controller 35 outputs the fluorescence image information $S_1$, which is output from the image-acquisition device 19, to the corrected fluorescence-image generating unit 25, and when the filter 32 is on the optical axis, the switching controller 35 outputs the white-light image information $S_2$ to the reflected-light image generating unit 24. Thus, the corrected fluorescence-image generating unit 25 generates the corrected fluorescence image $G_2$ using the fluorescence image information $S_1$ and the reference image information $S_3$ sent when the reference filter is on the optical axis.

By doing so, it is possible to select the most suitable wavelength band separately for the reference illumination light and the white light. For example, by selecting a band in which absorption by blood is low, such as 600 nm to 700 nm, it is possible to reduce inclusion of information about blood vessel structures in the reference image.

Figure 9:
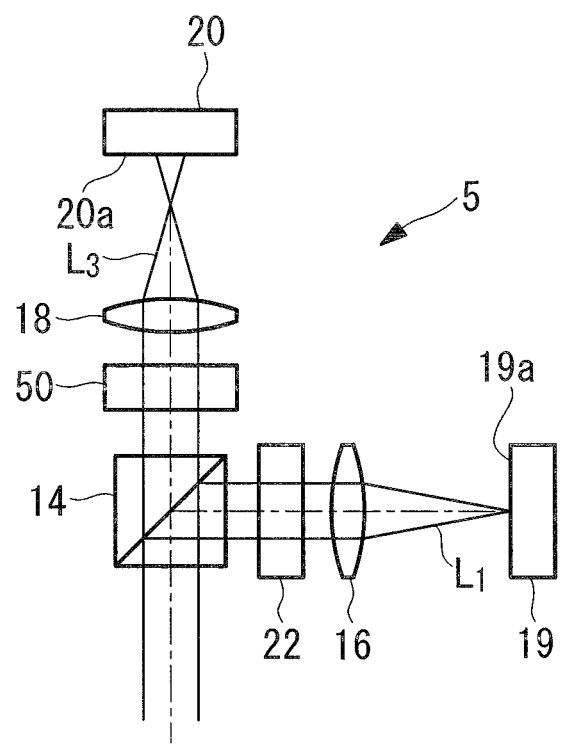
FIG. 9 is a schematic diagram showing a first modification of an image-acquisition unit in the fluoroscopy apparatus in FIG. 8.

At this time, although the reference illumination light returning from the observation target A is used as the reference image information $S_3$, by employing an optical system such as that in FIG. 9, fluorescence emitted from the observation target A, for example, autofluorescence, may be used instead. An autofluorescence-transmitting filter 50 that transmits only autofluorescence (for example, the wavelength band 500 nm to 630 nm) is disposed between the image-acquisition device 20 and the dichroic mirror 14. This design allows the reference filter to transmit light in a band that excites autofluorescence (for example, light in the wavelength band 400 to 470 nm). An autofluorescence image acquired when the reference filter is placed on the optical axis may be sent to the corrected fluorescence-image generating unit 25 to serve as the reference image information $S_3$.

With this arrangement, as in the case where the reflected white light is used, the problem of specularly reflected light at the surface of the observation target A being contained in the reference image information $S_3$ can be prevented, making it possible to obtain the reference image information $S_3$ using uniform autofluorescence from autofluorescent substances which are present substantially uniformly throughout the biological tissue serving as the observation target A. Therefore, it is possible to obtain a corrected fluorescence image $G_2$ having even higher quantitativeness.

Figure 10:
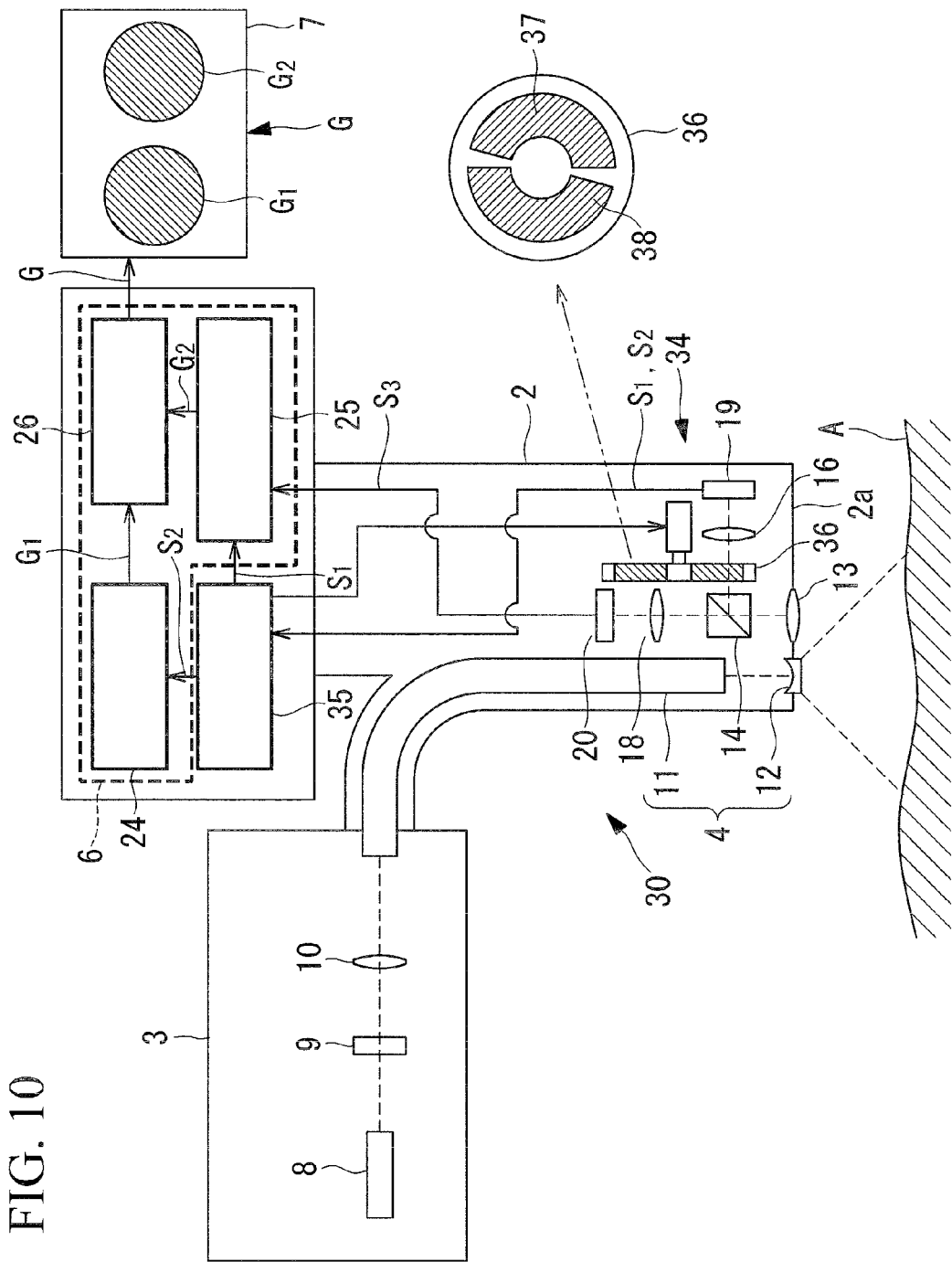
FIG. 10 is a diagram showing the overall configuration of a second modification of the image-acquisition unit in the fluoroscopy apparatus in FIG. 8.

In this embodiment, it is assumed that white light and excitation light are radiated in a time-division manner using the filter turret 31 disposed in the light source 3. Instead of this, however, as shown in FIG. 10, white light containing excitation light (for example, light in a wavelength band of 400 nm to 740 nm) may be constantly radiated from the light source 3, and fluorescence and white light may be acquired in a time-division manner by using a filter turret 36 provided in the image-acquisition unit 34.

The filter turret 36 is rotated so as to selectively change the filter disposed on the optical axis between a filter 37 that transmits white light (for example, light in a wavelength band of 400 nm to 700 nm) and a filter 38 that transmits fluorescence (for example, light in a wavelength band of 760 nm to 850 nm) while blocking other light.

In this case, when the filter turret 36 is disposed with the fluorescence-transmitting filter 38 disposed on the optical axis, the switching controller 35 outputs the fluorescence image information $S_1$, which is output from the image-acquisition device 19, to the corrected fluorescence-image generating unit 25. Also, when the white-light-transmitting filter 37 in the filter turret 36 is disposed on the optical axis, the switching controller 35 outputs the white-light image information $S_2$, which is output from the image-acquisition device 19, to the reflected-light image generating unit 24.

Figure 11:
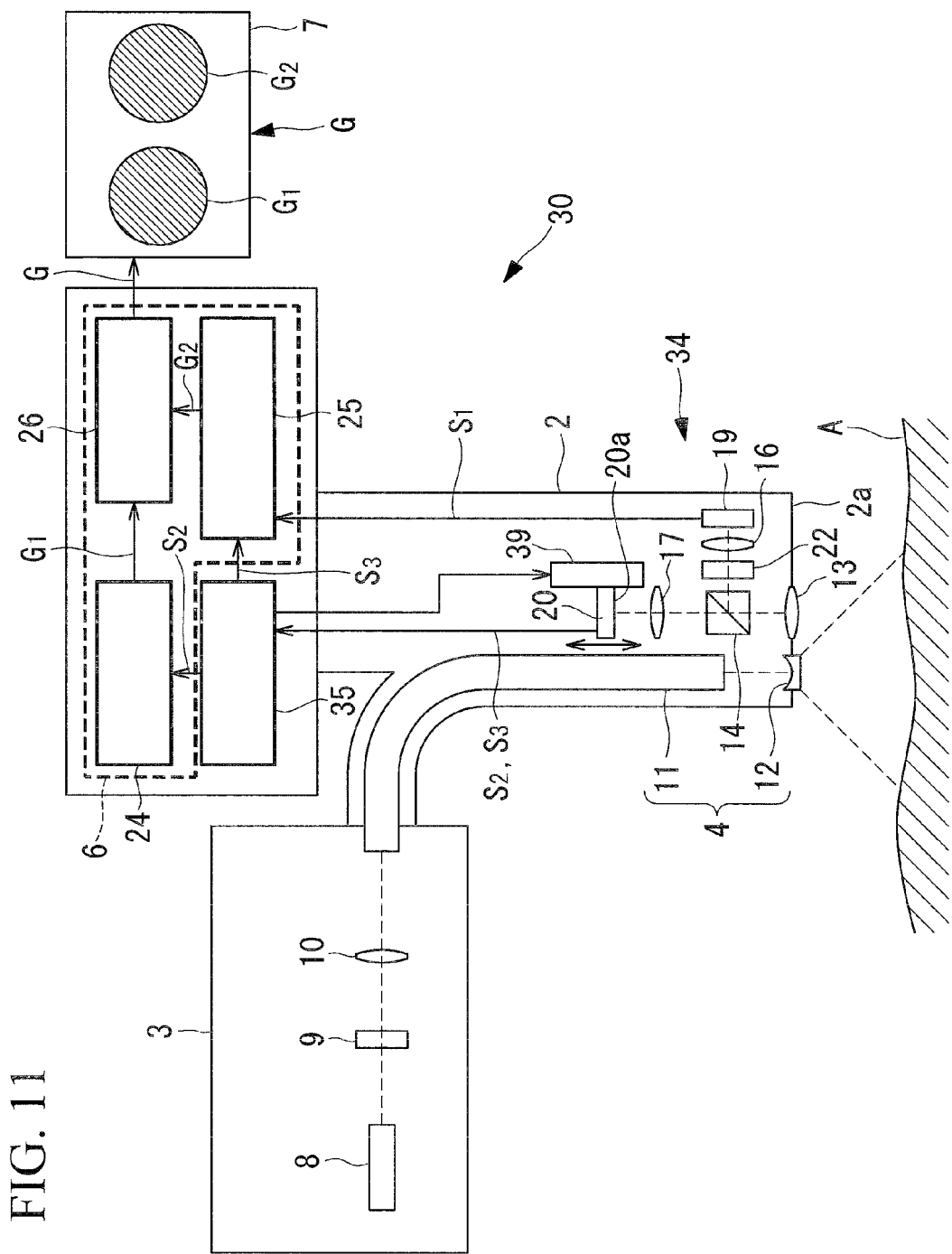
FIG. 11 is a diagram showing the overall configuration of a third modification of the image-acquisition unit in the fluoroscopy apparatus in FIG. 8.

Although the fluorescence image information $S_1$ and the white-light image information $S_2$ are acquired in a time-division manner by switching the wavelength of light transmitted by the filter turret 36, instead of this, as shown in FIG. 11, a moving mechanism 39 may be provided for moving, in the optical axis direction, the image-acquisition device 20 that acquires the white light transmitted through the dichroic mirror 14 between a position where the image-acquisition surface 20a is aligned with the focal position $P_2$ of the focusing lens 17 and a position shifted therefrom.

With this configuration, it is possible to alternately acquire the white-light image information $S_2$ and the reference image information $S_3$ in a time-division manner by driving the moving mechanism 39.

In this case, when the image-acquisition device 20 is disposed at a position where the image-acquisition surface 20a is aligned with the focal position $P_2$ of the focusing lens 17, the switching controller 35 sends the white-light image information $S_2$, which is output from the image-acquisition device 20, to the reflected-light image generating unit 24. On the other hand, when the image-acquisition device 20 is disposed at a position where the image-acquisition surface 20a is shifted relative to the focal position $P_2$ of the focusing lens 17, the switching controller 35 sends the reference image information $S_3$, which is output from the image-acquisition device 20, to the corrected fluorescence-image generating unit 25.

In the corrected fluorescence-image generating unit 25, the fluorescence image information $S_1$ that is constantly sent from the image-acquisition device 19 is divided by the reference-image information $S_3$ when it is received, generating the corrected fluorescence image $G_2$.

With this arrangement, because white light and fluorescence are captured with the different image-acquisition devices 19 and 20, it is possible to make only the image-acquisition device 19 that acquires fluorescence a high-sensitivity image-acquisition device, which enables fluoroscopy with improved accuracy as well as reduced cost.

Note that in this modification, it has been assumed that the white-light image information $S_2$ and the reference image information $S_3$ are alternately acquired in a time-division manner by driving the moving mechanism 39. Instead of this, however, it is possible to switch between a reflected-light observation mode and a fluorescence observation mode. In this case, when the reflected-light observation mode is selected, the moving mechanism 39 may be operated to move the image-acquisition device 20 so that the focal position $P_2$ of the focusing lens 17 is aligned with the image-acquisition surface 20a; whereas when the fluorescence observation mode is selected, the moving mechanism 39 may be operated to move the image-acquisition device 20 so that the focal position $P_2$ of the focusing lens 17 is disposed at a position shifted relative to the image-acquisition surface 20a.

Figure 12:
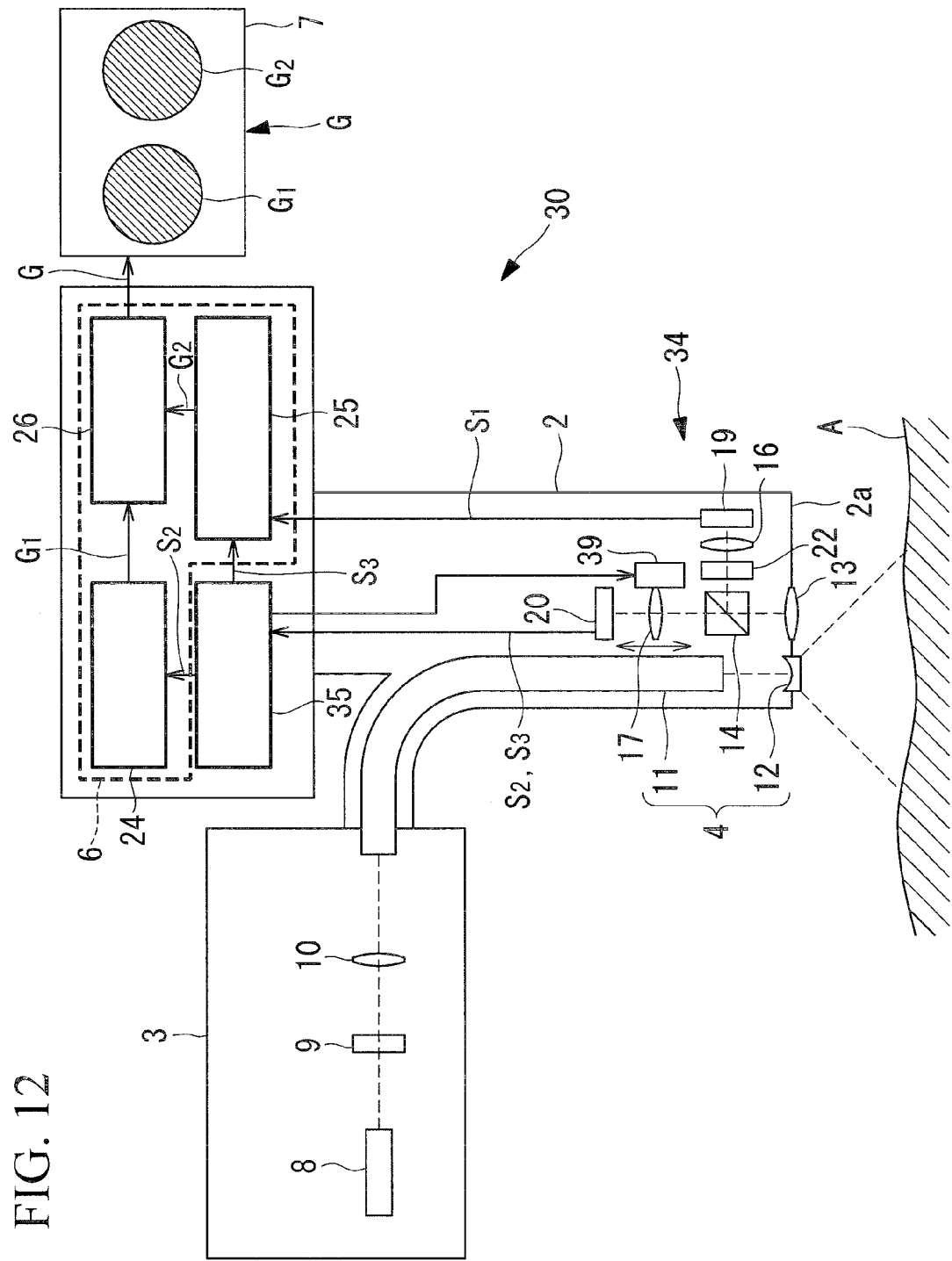
FIG. 12 is a diagram showing the overall configuration of a fourth modification of the image-acquisition unit in the fluoroscopy apparatus in FIG. 8.

In this modification, although the moving mechanism 39 moves the image-acquisition device 20 in the optical axis direction, instead of this, as shown in FIG. 12, it may move the focusing lens 17 in the optical axis direction. Moving the focusing lens 17 has the advantage that it is easier to move the focusing lens 17 than to move a member involving wiring, such as the image-acquisition device 20.

Figure 13:
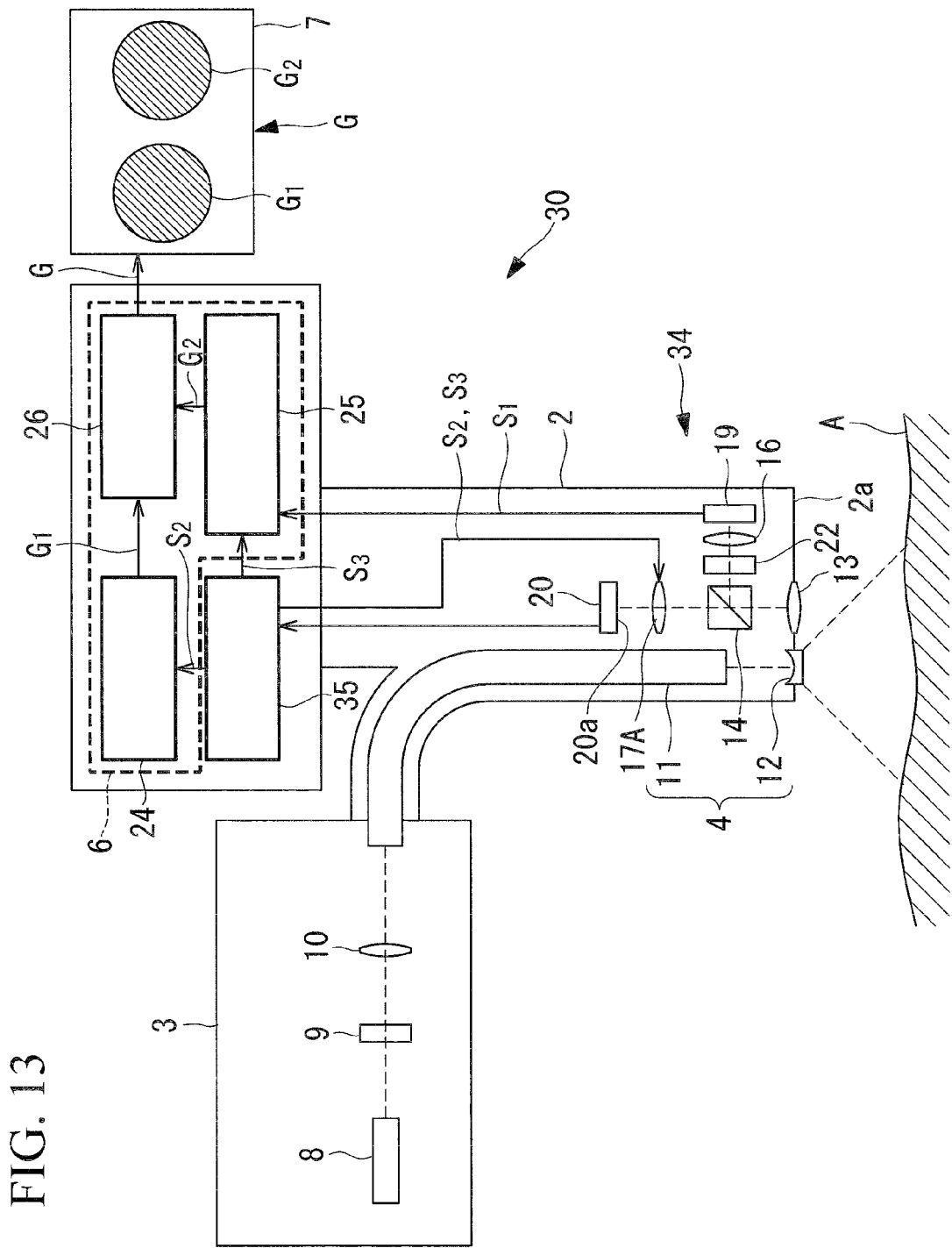
FIG. 13 is a diagram showing the overall configuration of a fifth modification of the image-acquisition unit in the fluoroscopy apparatus in FIG. 8.

Here it has been assumed that the focal position $P_2$ of the focusing lens 17 is moved relative to the image-acquisition surface 20a of the image-acquisition device 20 by moving the image-acquisition device 20 or the focusing lens 17 in the optical axis direction with the moving mechanism 39. Instead of this, however, as shown in FIG. 13, by using a liquid crystal lens 17A as the focusing lens 17 and adjusting the voltage applied thereto, the refractive index of the liquid crystal inside the liquid crystal lens 17A may be varied, thus causing the focal position $P_2$ to move in the optical axis direction. With this arrangement, the mechanical moving mechanism 39 is unnecessary, which has the advantages of a simple construction and improved responsiveness.

Figure 14:
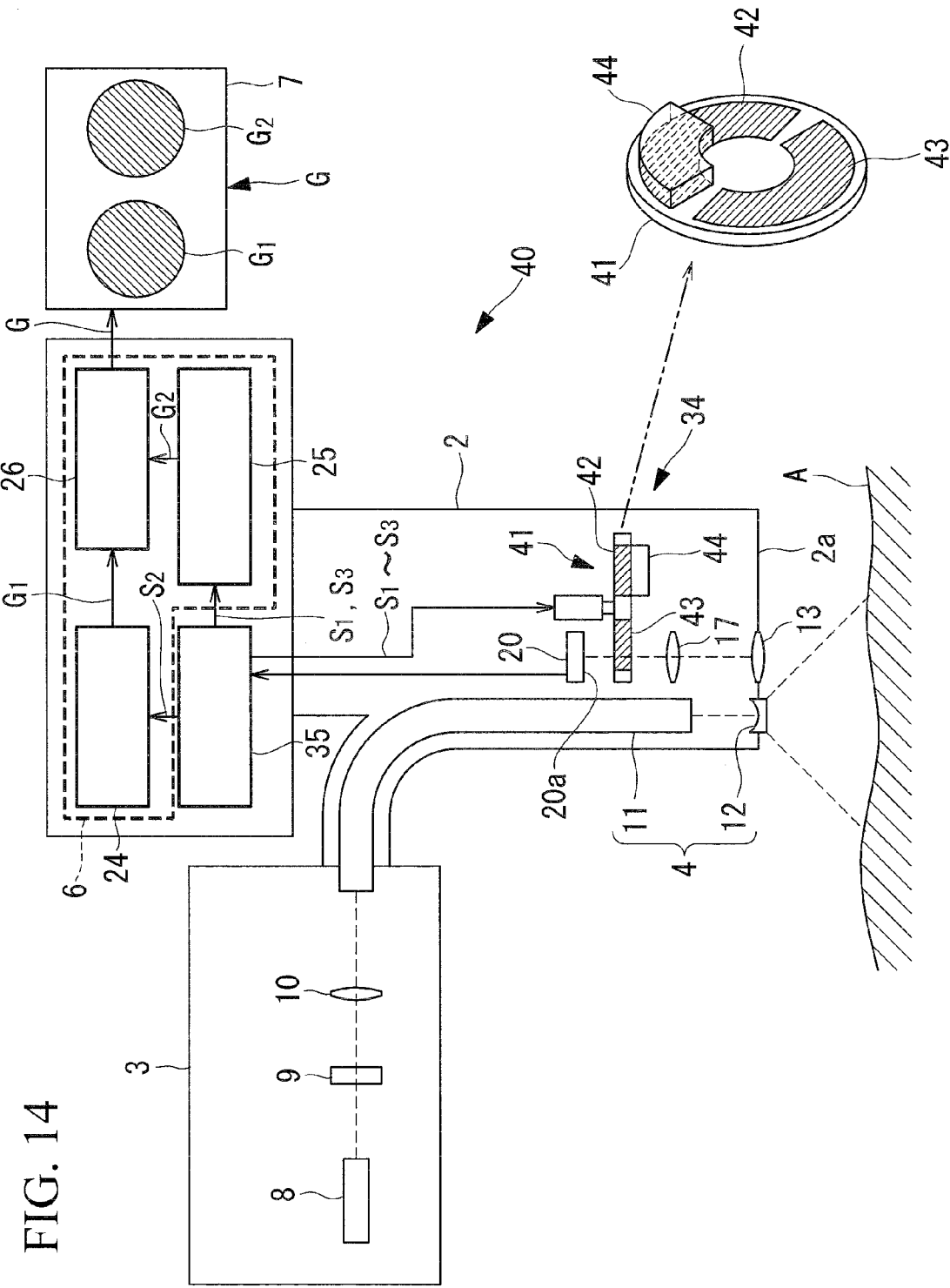
FIG. 14 is a diagram showing the overall configuration of a fluoroscopy apparatus according to a third embodiment of the present invention.

Next, a fluoroscopy apparatus 40 according to a third embodiment of the present invention will be described with reference to FIG. 14.

In the description of this embodiment, parts having the same configuration as those in the fluoroscopy apparatus 30 according to the second embodiment described above will be assigned the same reference numerals, and a description thereof will be omitted.

In the fluoroscopy apparatus 40 according to this embodiment, the dichroic mirror 14 and the half mirror 15 are not provided, and all of the returning light from the observation target A, collected via the objective lens 13, is focused by a single focusing lens 17 and is captured by a single image-acquisition device 20. In addition, a filter turret 41 that switches the wavelength of light transmitted therethrough is disposed between the focusing lens 17 and the image-acquisition device 20.

The filter turret 41 is provided with a filter 42 that transmits white light and a filter 43 that transmits fluorescence, and in addition, a parallel flat glass plate 44 is mounted to part of the filter 42 that transmits white light.

When the observation target A is irradiated with white light containing excitation light from the light source 3, returning light containing fluorescence and reflected white light returning from the observation target is collected by the objective lens 13.

In this state, in the filter turret 41, when the portion of the filter 42 that is not provided with the parallel flat glass plate 44 is disposed on the optical axis, the white-light image information $S_2$ is acquired by the image-acquisition device 20, and when the portion of the filter 42 provided with the parallel flat glass plate 44 is disposed on the optical axis, the reference image information $S_3$ is acquired by the image-acquisition device 20. Also, when the filter 43 is disposed on the optical axis, the fluorescence image information $S_1$ is acquired by the image-acquisition device 20.

All of the image information $S_1$ to $S_3$ from the image-acquisition device 20 are input to the switching controller 35, and in synchronization with the rotation of the filter turret 41, the white-light image information $S_2$ is output to the reflected-light image generating unit 24, and the fluorescence image information $S_1$ and the reference image information $S_3$ are both output to the corrected fluorescence-image generating unit 25.

Accordingly, reflected-light observation and fluorescence observation with high quantitativeness can be performed in a time-division manner with an extremely simple configuration using the single image-acquisition device 20 and the single focusing lens 17.

Note that, although the focal position $P_2$ is assumed to be shifted by the parallel flat glass plate 44 attached to the filter turret 41, instead of this, the moving mechanism 39 that moves the image-acquisition device 20 or the focusing lens 17 in the optical axis direction may be employed, or the focal position $P_2$ may be moved by using the liquid crystal lens 17A as the focusing lens 17.

The transmission wavelength of only the portion of the filter 42 that is provided with the parallel flat glass plate 44 may be changed; for example, it may be made to transmit only red light (600 nm to 700 nm). By selecting a band where absorption by blood is small in this way, it is possible to reduce the inclusion of information about blood vessel structures in the reference image.

Each of the embodiments described above has been described in terms of an example where an endoscope is used as the fluoroscopy apparatus. However, the present invention is not limited thereto and may be applied to any other type of fluoroscopy apparatus.

What is claimed is:

1. A fluoroscopy apparatus comprising:
   an illumination portion configured to irradiate an observation target with illumination light containing excitation light;
   a first image-acquisition section configured to acquire a fluorescence image in a prescribed observation region on the observation target;
   a second image-acquisition section configured to acquire an out-of-focus reference image of the observation target in the observation region; and
   an image correction section configured to correct the fluorescence image acquired by the first image-acquisition section using the reference image acquired by the second image-acquisition section;
   wherein the image correction section is configured to divide the fluorescence image by the reference image, and wherein the fluorescence image that is divided is not dependent on the distance and angle of the illumination light, and wherein an image acquisition device acquires the reference image, and wherein the image acquisition device is located outside the depth of focus of the second image-acquisition section.

2. A fluoroscopy apparatus according to claim 1, wherein:
   the second image-acquisition section comprises an image-acquisition device configured to acquire the reference image, and an image-acquisition optical system configured to focus light returning from the observation target; and
   an image-acquisition surface of the image-acquisition device is disposed at a position shifted in an optical axis direction relative to a focal position of the image-acquisition optical system.

3. A fluoroscopy apparatus according to claim 2, further comprising a moving mechanism configured to move the image-acquisition optical system or the image-acquisition device in the optical axis direction.

4. A fluoroscopy apparatus according to claim 1,
   wherein the illumination portion irradiates the observation target simultaneously with white light and excitation light, serving as the illumination light;
   the fluoroscopy apparatus further comprises
   a light-collecting lens configured to collect the return light returning from the observation target;
   a first splitting portion configured to split fluorescence and white light from the returning light collected by the light-collecting lens;
   a second splitting portion configured to further split the white light split by the first splitting portion;
   a white-light image-acquisition optical-system configured to focus one of the white light beams split by the second splitting portion; and
   a white-light image-acquisition device whose image-acquisition surface is disposed at a focal position of the white-light image-acquisition optical system;
   wherein the fluorescence split by the first splitting portion is guided to the first image-acquisition section, and
   wherein the other white light beam split by the second splitting portion or light in part of a wavelength band of the other white light beam is guided to the second image-acquisition section.

5. A fluoroscopy apparatus according to claim 4, wherein the second image-acquisition section comprises a reference-light image-acquisition optical system whose focal position is shifted in the optical axis direction relative to the image-acquisition surface of the white-light image-acquisition device.

6. A fluoroscopy apparatus according to claim 1,
   wherein the illumination portion irradiates the observation target with white light and excitation light, serving as the illumination light, in a time-division manner;
   the fluoroscopy apparatus further comprises
   a light-collecting lens configured to collect the return light returning from the observation target; and
   a splitting portion configured to split the return light collected by the light-collecting lens into two;
   wherein one of the returning light beams split by the splitting portion is guided to the first image-acquisition section;
   wherein the other returning light beam split by the splitting portion is guided to the second image-acquisition section; and
   wherein the first image-acquisition section acquires a white-light image when the white light is radiated from the illumination portion and acquires a fluorescence image when the excitation light is radiated from the illumination portion.

7. A fluoroscopy apparatus according to claim 6, wherein the illumination portion further irradiates the observation target with reference illumination light in a time-division manner.

8. A fluoroscopy apparatus according to claim 1,
   wherein the illumination portion irradiates the observation target with white light and excitation light, serving as the illumination light, in a time-division manner,
   the fluoroscopy apparatus further comprises:
   a light-collecting lens configured to collect the returning light returning from the observation target; and
   a splitting portion configured to split the returning light collected by the light-collecting lens into white light and fluorescence;
   wherein the fluorescence split by the splitting portion is guided to the first image-acquisition section;
   wherein the white light split by the splitting portion is guided to the second image-acquisition section; and
   wherein the second image-acquisition section includes an image-acquisition device configured to acquire the reference image and a white-light image, an image-acquisition optical system configured to focus the white light returning from the observation target, and a switching mechanism configured to selectively switch the focal position of the image-acquisition optical system between a position in alignment with and a position shifted relative to an image-acquisition surface of the image-acquisition device when the white light is radiated by the illumination portion.

9. A fluoroscopy apparatus according to claim 1,
wherein the illumination portion irradiates the observation target with reference illumination light, white light, and excitation light, serving as the illumination light, in a time-division manner,
the fluoroscopy apparatus further comprises:
a light-collecting lens that collects the returning light returning from the observation target; and
a splitting portion that splits the returning light collected by the light-collecting lens into white light and fluorescence;
wherein the fluorescence split by the splitting portion is guided to the first image-acquisition section;
wherein the white light split by the splitting portion is guided to the second image-acquisition section;
wherein the second image-acquisition section includes
an image-acquisition device configured to acquire the reference image and a white-light image;
an image-acquisition optical system configured to focus the white light returning from the observation target; and
the illumination portion further irradiates the observation target with the reference illumination light in a time division manner;
wherein a switching mechanism configured to switch between a position where the focal position of the image-acquisition optical system is aligned with an image-acquisition surface of the image-acquisition device when the white light is radiated by the illumination portion, and a position where the focal position of the image-acquisition optical system is shifted relative to the image-acquisition surface of the image-acquisition device when the reference illumination light is radiated by the illumination portion.

10. A fluoroscopy apparatus according to claim 1,
wherein the illumination portion illuminates the observation target with white light and excitation light, serving as the illumination light, either simultaneously or individually as selected;
the fluoroscopy apparatus further comprises:
a light-collecting lens configured to collect returning light returning from the observation target; and
a splitting portion configured to split the returning light collected by the light-collecting lens into white light and fluorescence;
wherein the fluorescence split by the splitting portion is guided to the first image-acquisition section;
wherein the white light split by the splitting portion is guided to the second image-acquisition section; and
wherein the second image-acquisition section includes an image-acquisition device configured to acquire the reference image and a white-light image, an image-acquisition optical system configured to focus the white light returning from the observation target, and a switching mechanism configured to selectively switch the focal position of the image-acquisition optical system between a position aligned with and a position shifted relative to an image-acquisition surface of the image-acquisition device.

11. A fluoroscopy apparatus according to claim 8, wherein the switching mechanism is a moving mechanism configured to move the image-acquisition optical system or the image-acquisition device in the optical axis direction.

12. A fluoroscopy apparatus according to claim 8, wherein the image-acquisition optical system is a liquid-crystal lens.

13. A fluoroscopy apparatus according to claim 1,
wherein the illumination portion irradiates the observation target with white light and excitation light simultaneously,
the fluoroscopy apparatus further comprises:
an image-acquisition optical system configured to focus returning light returning from the observation target;
a filter portion that selectively transmits the reference light, the white light, or fluorescence in the returning light;
an image-acquisition device configured to acquire the reference light, the white light, or the fluorescence transmitted through the filter portion;
a switching mechanism configured to switch between a position where the focal position of the image-acquisition optical system is aligned with an image-acquisition surface of the image-acquisition device when the white light is transmitted by the filter portion, and a position where the focal position of the image-acquisition optical system is shifted relative to the image-acquisition surface of the image-acquisition device when the reference light is transmitted; and
an image correction section configured to correct the fluorescence image acquired by the image-acquisition device using the reference image acquired when the reference light is transmitted by the switching mechanism.

14. A fluoroscopy method comprising:
an illumination step of irradiating an observation target with illumination light containing excitation light;
a fluorescence-image acquisition step of acquiring a fluorescence image in a prescribed observation region of the observation target;
a reference-image acquisition step of acquiring an out-of-focus reference image of the observation target in the observation region; and
an image correcting step of correcting the fluorescence image acquired in the fluorescence-image acquisition step using the reference image acquired in the reference-image acquisition step;
wherein the image correction section comprises dividing the fluorescence image by the reference image, and wherein the fluorescence image that is divided is not dependent on the distance and angle of the illumination light, and wherein an image acquisition device acquires the reference image, and wherein the image acquisition device is located outside the depth of focus of the second image-acquisition section.

15. A fluoroscopy apparatus according to claim 9, wherein the switching mechanism is a moving mechanism configured to move the image-acquisition optical system or the image-acquisition device in the optical axis direction.

16. A fluoroscopy apparatus according to claim 10, wherein the switching mechanism is a moving mechanism configured to move the image-acquisition optical system or the image-acquisition device in the optical axis direction.

17. A fluoroscopy apparatus according to claim 9, wherein the image-acquisition optical system is a liquid crystal lens.

18. A fluoroscopy apparatus according to claim 10, wherein the image-acquisition optical system is a liquid crystal lens.

* * * * *